US006469061B1

United States Patent
Flescher et al.

(10) Patent No.: US 6,469,061 B1
(45) Date of Patent: Oct. 22, 2002

(54) JASMONATE PHARMACEUTICAL COMPOSITION FOR TREATMENT OF CANCER

(75) Inventors: Eliezer Flescher, Hod Hasharon; Orit Fingrut, Kfar-Sava, both of (IL)

(73) Assignee: Ramot University Authority for Applied Research and Industrial Development Limited, Tel Aviv (IL)

( * ) Notice: Subject to any disclaimer, the term of this patent is extended or adjusted under 35 U.S.C. 154(b) by 0 days.

(21) Appl. No.: 09/825,347

(22) Filed: Apr. 4, 2001

(51) Int. Cl.$^7$ .............................................. A01N 37/02
(52) U.S. Cl. ..................................... 514/530; 514/573
(58) Field of Search .................................. 514/573, 530

(56) References Cited

U.S. PATENT DOCUMENTS

| 5,118,711 A | 6/1992 | Wilson et al. |
| 5,436,226 A | 7/1995 | Lulai et al. |
| 6,114,284 A | 9/2000 | Fujisawa et al. |

OTHER PUBLICATIONS

Seiki et al, Chemical Abstracts, vol. 126, #196471h, 1998.*
Okano et al, Chemical Abstracts, vol. 127, #200188v, 1997.*
(1) "Mechanisms of Apoptosis: Integration of Genetic, Biochemical, and Cellular Indicators", Bernard W. Stewart, *Journal of the National Cancer Institute*, vol. 86, No. 17, Sep. 7, 1994, pp. 1286–1295.
(2) "Sodium Salicylate Activates Caspases and Induces Apoptosis of Myeloid Leukemia Cell Lines", Lidija Klampfer et al, *Blood*, vol. 93, No. 7 (Apr. 1), 1999, pp. 2386–2394.
(3) Emerging Roles of Caspass–3 in Apoptosis, Porter et al, *Cell Death and Differentiation*, (1999), pp. 99–104.
(4) "Cell–Type–Specific Activation of c–Jun N–Terminal Kinase by Salicylates", Schwenger et al; *Journal of Cellular Physiology*, 179, (1999), pp. 109–114.
(5) "Sodium Salicylate Induces Apoptosis Via p38 Mitogen–Activated . . .", Schwenger et al, *Proc. Natl. Acad. Sci USA*, (1997), pp. 2869–2873.
(6) "Cytochemical Methods for the Detection of Apoptosis", Willingham, *The Journal of Histochemistry & Cytochemistry*, vol. 47, pp. 1101–1109.
(7) "Sacrifice in the Face of Foes: Pathogen–Induced Programmed Cell Death in Plants", Mittler et al, *Trends in Microbiology*, vol. 47, No. 1, Jan. 1996, pp. 10–15.
(8) "Death Dont't Have No Mercy: Cell Death Programs in Plant–Microbe Interactions", Dangl et al, *The Plant Cell*, vol. 8, Oct. 1996, pp. 1793–1807.
(9) "Interplant Communication: Airborne Methyl Jasmonate Induces Synthesis of Proteinase Inhyibitors in Plant Leaves", Farmer et al, *Proc. Natl. Acad. Sci. USA*, vol. 87, Oct. 1990, pp. 7713–7716.

(10) "The Biochemistry and the Physiological and Molecular Actions of Jasmonates", Sembdner et al, *Annu. Rev. Physiol. Plant. Mol. Biol.*, Sembdner et al, (1993), pp. 569–589.
(11) "Systemic Acquired Resistance", Ryals et al, *The Plant Cell*, Vol. 8, Oct. 1996, pp. 1809–1819.
(12) "Prostaglandins in the Treatment of Cancer", Sasaki et al, *Anti–Cancer Drugs*, (1994), vol. 5, pp. 131–138.
(13) "Inhibition of $G_1$Cyclin–Dependent Kinase Activity . . . ", Gorospe et al, *Molecular and Cellular Biology*, Mar. 1996, pp. 762–770.
(14) "Comparative Anti–Viral and Anti–Proliferative Activity . . . ", D'Onofrio et al, *Int. J. Cancer*, 51, (1992), pp. 481–488.
(15) "Natural Resistance of Acute Myeloid Leukemia Cell Lines to Mitoxantrone is Associated with Lack of Apoptosis", Bailly et al, *Leukemia*, (1997) 11, pp. 1523–1532.
(16) "An International Evaluation of the Cancer–Preventive Potential of Nonsteroidal Anti–Inflammatory Drugs", Vainio et al, *Cancer Epidemoil. Biomarkers & Prevention*, Sep. 1997, vol. 6, pp. 749–753.
(17) "Arachidonic Acid Metabolism", Needleman et al, *Ann. Rev. Biochem.*, 1986, 55, pp. 69–102.
(18) "The Octadecanoid Signalling Pathway in Plants Mediates a Response to Ultraviolet Radiation", Conconi et al, *Nature*, vol. 383, Oct. 31, 1996, pp. 826–829.

(List continued on next page.)

Primary Examiner—James H. Reamer
(74) Attorney, Agent, or Firm—Lowe Hauptman Gilman & Berner, LLP

(57) ABSTRACT

A pharmaceutical composition useful for the treatment of cancer in mamnmals, comprising as the active ingredient a therapeutically effective amount of a jasmonate of the formula:

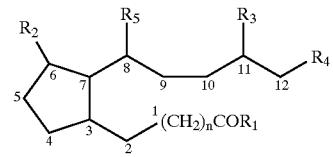

wherein:
  n is 0,1, or 2; $R_1$ is OH, alkoxy, O-glucosyl, or imino; $R_2$ is OH, O, alkoxy or O-glucosyl; $R_3$, $R_4$ and $R_5$ are H, OH, alkoxy or O-glucosyl; and/or wherein $R^1$ and $R_2$, or $R^1$ and $R_4$ together form a lactone; and further wherein the bonds between $C_3:C_7$, $C_4:C_5$, and $C_9:C_{10}$ may be double or single bonds; or a derivative of said formula; the derivative having at least one of the following: a lower acyl side chain at $C_3$ (free acid, ester or conjugate); a keto or hydroxy (free hydroxy or ester) moiety at the $C_6$ carbon; or an n-pentenyl or n-pentyl side chain at $C_7$. These jasmonates are useful in treating a wide variety of malignancies.

32 Claims, 6 Drawing Sheets

OTHER PUBLICATIONS

(19) "Long-Term Use of Nonsteroidal Antiinflammatory Drugs and Other Chemopreventors and Risk of Subsequent Colorectal Neoplasia", Peleg et al, *Digestive Diseases and Sciences*, vol. 41, No. 7 (Jul. 1996), pp. 1319–1326.

(20) "Non-Steroidal Anti-Inflammatory Drugs and the Chemoprevention of Colorectal and Oesophageal Cancers", *Gut*, 1996, 38, pp. 646–648.

(21) "Salicylates Inhibit NF–KB Activation and Enhance TNF . . . ", McDade et al, *Journal of Surgical Research*, 83, (1999) pp. 56–61.

(15) Basaria et al., "Clinical Review 138, Anabolic–Androgenic Steroid Therapy in Treatment of Chronic Diseases." Journal of Clinical Endocrinology and Metabolism, 86(11):5108–5117, Nov. 2001.

* cited by examiner

Table 1: Effects of plant stress hormones on normal and transformed human cells.

| Cell type | Salicylic acid | | Jasmonic acid | | Methyl jasmonate | |
|---|---|---|---|---|---|---|
| Molt-4 | +++ | SP* | +++++ | CD‡ | +++++ | CD |
| LNCaP | +++ | SP | +++ | SP | ++++ | CD |
| MCF-7 | +++ | SP | ++ | SP | +++ | CD |
| SK 28 | +++ | SP | ++++ | SP | +++ | CD |
| Normal Lymph. | | − | | − | | − |

*SP= suppression of cell proliferation

‡CD= cell death

+ =number of "+" signs represents the extent of the cytotoxic effect.

− =no effect

JASMONATE PHARMACEUTICAL COMPOSITION FOR TREATMENT OF CANCER

FIELD OF THE INVENTION

The present invention relates to a pharmaceutical composition for use in treatment of a wide variety of malignancies in mammals. The composition of the present invention is non-toxic and targets cancer cells, as opposed to healthy peripheral cells.

BACKGROUND OF THE INVENTION

Plants may undergo instances of stress, which result in activation of complex genetic pathways that bring about physiological responses appropriate to the stress source. Common stresses to which plants are subjected include extreme UV radiation, osmotic shock, heat shock and pathogen attack. Stress hormones have evolved in plants, which are released in such times of stress and initiate various cascades which end in appropriate responses. Jasmonic acid (JA) and methyl jasmonate (MJ), belong to the group of natural plant stress hormones named "jasmonates" (Sembdner and Parthier, Annu. Rev. Physiol. Plant Mol. Biol., 44, 569–589, 1993). Jasmonic acid is crucial to intracellular signaling in response to injury and methyl jasmonate causes induction of a proteinase inhibitor that accumulates at low concentrations in response to wounding or pathogenic attacks (Farmer and Ryan, Proc. Natl. Acad. Sci., 87, 7713–7716, 1990). Jasmonates have been patented for a variety of uses in plant growth and crop improvement. Application of jasmonates can have a wide range of contradictory effects on virtually all plants. These effects range from inhibition of plant development to promotion of plant processes. U.S. Pat. No. 6,114,284 discloses use of jasmonic acid ester and giberellin to synergistically enhance plant growth and development. U.S. Pat. No. 5,436,226 discloses use of a jasmonate to inhibit sprouting and darkening in tubers after they have been picked, and U.S. Pat. No. 5,118,711 discloses use of methyl jasmonate to repel insects.

Sodium salicylate (SA) is a plant stress hormone of another family, and a central mediator of plant defense responses to pathogens and to injury (Ryals et al., Plant Cell., 8, 1809–1819, 1996).

One response to attack by a microbial pathogen, may be, for instance, programmed cell death termed the hypersensitive response (HR) which results in the formation of a zone of dead cells around the infection site. The layers of dead cells that surround the site of pathogen entry are thought to function as a physical barrier that inhibits further proliferation and spread of the pathogen. A subsequent step of the process involves synthesis of the plant stress hormone sodium salicylate, and accumulation of antimicrobial agents, such as pathogenesis-related proteins and phytoalexins (Dangl et al., Plant Cell, 8, 1793–1807, 1996; Mitler and Lam, Trends. Microbiol., 4, 10–15 1996).

This programmed cell death in response to pathogen attack is reminiscent of programmed cell death known to occur in mammalian cells. Mammalian cells can die by "unscheduled" necrosis, which is caused by outside damage and results in cell explosion, or in the more organized manner of apoptosis, also termed "programmed cell death" or "cellular suicide" (Willingham, J. Histochem. Cytochem., 47, 1101–1109, 1999). In apoptosis, biochemical and morphological events are usually organized in a cascade of very specific and controlled steps, which include fragmentation of the nucleus and shrinkage of the cell, and end with complete splitting of the cell contents to apoptotic bodies (Stewart, J. Cancer Inst., 86, 1286–1295, 1994).

The process of apoptosis is slower then necrosis and happens in a few hours or days, depending on the inducer. This kind of death may be regarded as "cell suicide" (Willingham, J. Histochem. Cytochem., 47, 1101–1109, 1999).

Surprisingly enough, the plant stress hormone SA was able to induce intracellular biochemical events typical of a stress response in mammalian cells as well (Schwenger et al., Proc. Natl. Acad. Sci. USA, 4, 2869–2873, 1997; Schwenger et al., J. Cell. Physiol., 179, 109–114, 1999), and was able to induce apoptosis (programmed cell death) in cell lines of human myeloid leukemia, through activation of Caspase-3 (a mammalian cytoplasmic protease essential for the final steps of apoptosis) (Klampfer et al., Blood., 93, 2386–2394, 1999; Willingham, J. Histochem. Cytochem., 47, 1101–1109, 1999; Porter and Janicke, Cell Death Differ., 6, 99–104 1999). SA was likewise able to induce apoptosis in mammalian FS-4 fibroblasts (Schwenger et al., Proc. Natl. Acad. Sci. USA, 4, 2869–2873, 1997), and in human pancreatic cancer (McDade et al., J. Surg. Res., 83, 56–61 1999). The family of drugs of which salicylic acid is a member, non-steroidal anti-inflammatory drugs (NSAID), have potent chemopreventive activity (Morgan, Gut., 38, 646–648 1996; Peleg et al., Dig. Dis. Sci., 41, 1319–1326 1996; Vainio et al., Cancer Epidemiol. Biomarkers Prev., 6, 749–753, 1997).

Many plant genes that respond to environmental and developmental changes are regulated by jasmonic acid, which is derived from linolenic acid by an octadecanoid pathway. Plant defense responses to certain wavelengths of ultraviolet radiation require activation of the octadecanoid defense signaling pathway (Conconi et al., Nature, 383, 826–829, 1996). The release of linolenic acid from the membrane into the cell, and its subsequent conversion to JA, is analogous to signaling pathways in mammalian cells, where releasing of arachidonic acid from the membrane results in synthesis of eicosanoids, such as prostaglandins (Needleman et al., Ann. Rev. Biochem., 55, 69–102 1986). Prostaglandins of the A and J series, which contain a cyclopentanone ring structure, are potent inhibitors of cell proliferation in vitro and are able to suppress tumorigenicity in vivo (D'Onofrio et al., Int. J. Cancer., 51, 481–488, 1992; Gorospe et al., Mol. Cell. Biol., 16, 762–770, 1996). The ability of prostaglandins to arrest growth in a diverse range of tumor cell lines has raised the possibility that they might be useful for treatment of human cancer (Sasaki and Fukushima, Anti-Cancer Drugs, 5, 131–138, 1994). Structural similarity exists between jasmonates and prostaglandins, since both are cyclopentanons, which suggests that JA and MJ may be potent against cancer cells.

The present invention discloses use of members of the plant stress hormone family termed "jasmonates", for suppressing and killing mammalian cancer cells that represent major types of human malignancies. To the best of the applicant's knowledge, jasmonates were never studied as anti-cancer agents. Since chemotherapeutic drugs for use in mammalian systems usually work by induction of apoptosis in cancer cells (Bailly et al., Leukemia., 11, 1523–1532, 1997), and jasmonates are thought to be involved in an apoptotic response to plant stress, the applicants tested the ability of jasmonates to suppress replication of mammalian cancer cell lines of clinical importance. The cytotoxicity of jasmonates was compared to that of the plant stress hormone sodium salicylate, which is known to be cytotoxic to mammalian cancer cells.

Chemotherapeutic drugs are often so highly toxic as to leave the patient with numerous side-effects that seriously diminish the patient's quality of life and impair his function. Chemotherapy regimens can last several months and can be performed repeatedly in cases of relapse, leaving even an ambulatory patient with repeated periods of partial impairment of function. The need exists, therefore, for chemotherapeutic drugs with undiminished potency, yet with a higher degree of specificity towards malignant cells, and fewer side-effects. The present invention discloses use of jasmonate compounds to treat malignancies. Jasmonates are commonly found in minute quantities in many edible plants (Sembdner and Parthier, Annu. Rev. Physiol. Plant Mol. Biol., 44, 569–589 1993), such as tomato, potato, and pumpkin seeds, and thus are non-toxic. Jasmonates are shown by the applicants to be highly specific; inducing apoptosis in clinically important types of cancer cells, yet not effecting the proliferation of normal human cells, such as healthy lymphocytes. Jasmonates are additionally shown by the applicants to be effective in the treatment of lymphoma in a cancer model in mice.

It is the object of the present invention to propose jasmonate compounds as a potent chemotherapeutic drug, with a high degree of specificity towards malignant cells. These and other objects of the present invention will become more apparent from the detailed description of the preferred embodiments, that follows below.

In the present invention, the term "jasmonates" is intended to include the natural plant hormones jasmonic acid and methyl jasmonate, as well as any natural or synthetic derivative and isomers of jasmonic acid and of jasmone. These derivatives have:

1) a lower acyl side chain at $C_3$ (free acid or ester or conjugate)
2) a keto or hydroxy (free hydroxy or ester) moiety at the $C_6$ carbon
3) an n-pentenyl or n-pentyl side chain at $C_7$.

A variety of jasmonates may be used, and include but are not limited to those having the formula:

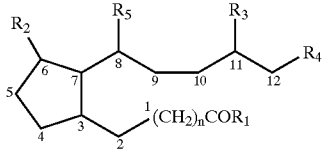

wherein n is 0,1, or 2;

$R_1$ is OH, alkoxy, O-glucosyl, or imino, $R_2$ is OH, O, alkoxy or O-glucosyl, $R_3$, $R_4$ and $R_5$ are H, OH, alkoxy or O-glucosyl, and/or wherein $R_1$ and $R_2$, or $R_1$ and $R_4$ together form a lactone, and further wherein the bonds between $C_3$:$C_7$, $C_4$:$C_5$, and $C_9$:$C_{10}$ may be double or single bonds.

SUMMARY OF THE INVENTION

The present invention relates to a pharmaceutical composition useful for the treatment of cancer in mammals, comprising as an active ingredient a therapeutically effective amount of a jasmonate compound of the formula I:

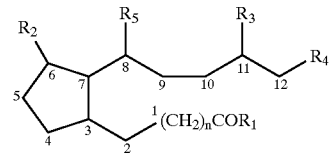

Formula I wherein:

n is 0,1, or 2;

$R_1$ is OH, alkoxy, O-glucosyl, or imino, $R_2$ is OH, O, alkoxy or O-glucosyl, $R_3$, $R_4$ and $R_5$ are H, OH, alkoxy or O-glucosyl, and/or wherein $R_1$ and $R_2$, or $R_1$ and $R_4$ together form a lactone, and further wherein the bonds between $C_3$:$C_7$, $C_4$:$C_5$, and $C_9$:$C_{10}$ may be double or single bonds; or a derivative of said formula, wherein the derivative has at least one of the following:

a lower acyl side chain at $C_3$ (free acid or ester or conjugate), a keto or hydroxy (free hydroxy or ester) moiety at the $C_6$ carbon, or an n-pentenyl or n-pentyl side chain at $C_7$.

According to a preferred embodiment of the present invention, the jasmonate is selected from methyl jasmonate, jasmonic acid, jasmone, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 6-epi-cucurbic-acid-lactone, 12-hydroxy-jasmonic acid, 12-hydroxy-jasmonic-acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydrojasmonic acid, 6,7-didehydrojasmonic acid, 7,8-didehydrojasmonic acid, cis-jasmone, methyldihydroisojasmonate, dihydro-jasmone, amino acid conjugates of jasmonic acid, and the lower alkyl esters, the carrier ligand conjugates and the sterioisomers thereof.

Further, according to a preferred embodiment of the present invention, the cancer to be treated is selected from prostate cancer, breast cancer, skin cancer, colon cancer, lung cancer, pancreatic cancer, lymphoma, leukemia, head and neck cancer, kidney cancer, ovarian cancer, bone cancer, liver cancer or thyroid cancer.

Moreover, in accordance with a preferred embodiment of the present invention, the active ingredient is dissolved in any acceptable lipid carrier.

Still further, in accordance with a preferred embodiment of the present invention, the composition additionally comprises at least one other chemotherapeutic agent.

Additionally in accordance with a preferred embodiment of the present invention the composition is prepared for oral administration. In such embodiments, the composition is in a form selected from an emulsion, a solution, a capsule, a tablet.

In another embodiment of the present invention, the composition is prepared for administration by injection. The composition is prepared so as to be suitable for injection intra-muscularly, intra-peritoneally, or intraveneously.

Still further, in certain embodiments, the composition is prepared for topical administration. According to these embodiments, the composition is in a form selected from an ointment, a gel, or a cream.

Moreover, in some embodiments of the present invention, the composition is prepared for administration by inhalation. In other embodiments, the composition is prepared for administration via a suppository.

The present invention further provides a method for treatment of cancer in mammals, comprised of administering a pharmaceutical composition containing as the active ingredient a therapeutically effective amount of a jasmonate compound of Formula I:

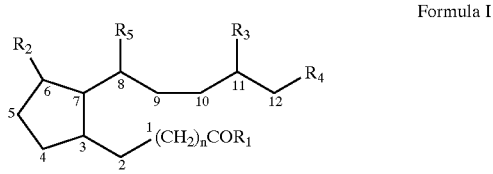

Formula I wherein:

n is 0, 1, or 2;

$R_1$ is OH, alkoxy, O-glucosyl, or imino, $R_2$ is OH, O, alkoxy or O-glucosyl, $R_3$, $R_4$ and $R_5$ are H, OH, alkoxy or O-glucosyl, and/or wherein $R_1$ and $R_2$, or $R_1$ and $R_4$ together form a lactone, and further wherein the bonds between $C_3:C_7$, $C_4:C_5$, and $C_9:C_{10}$ may be double or single bonds; or a derivative of said formula, wherein the derivative has at least one of the following:
 a lower acyl side chain at $C_3$ (free acid or ester or conjugate), a keto or hydroxy (free hydroxy or ester) moiety at the $C_6$ carbon, or an n-pentenyl or n-pentyl side chain at $C_7$.

BRIEF DESCRIPTION OF THE DRAWINGS

The present invention is herein described, by way of example only, with reference to the accompanying drawings, wherein.

Table 1 is a comparison of the level of toxicity effected by jasmonic acid, methyl jasmonate and salicylic acid on four malignant cell lines.

FIG. 2 is a graph illustrating the activity levels of the apoptotic marker protein Caspase-3, in Molt-4 cells treated with jasmonic acid and methyl jasmonate.

Figure 3:
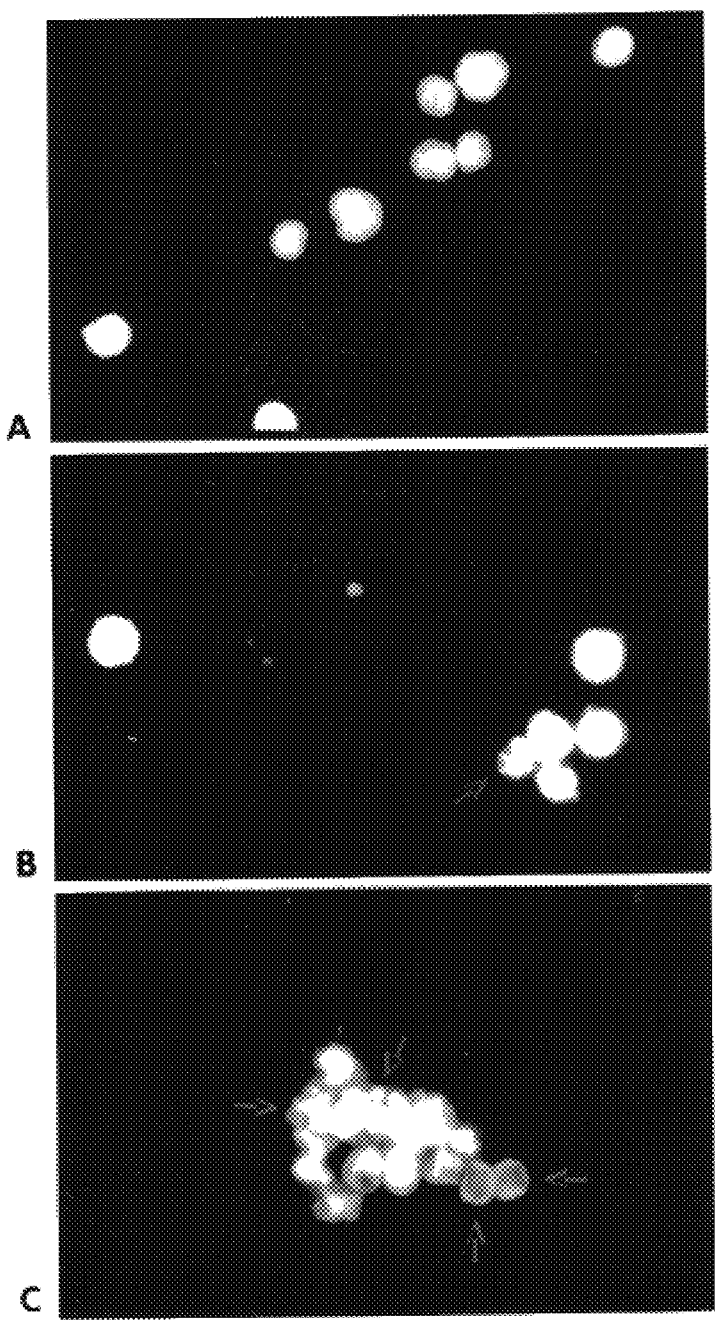

FIG. 3 illustrates fluorescence microscopy pictures depicting apoptotic changes in morphology of Molt-4 cells, after treatment with jasmonic acid and methyl jasmonate.

FIG. 4 is a graph illustrating the specificity of the cytotoxic effect jasmonates exert on malignant cells, versus no effect on normal lymphocytes from healthy donors.

Figure 5:
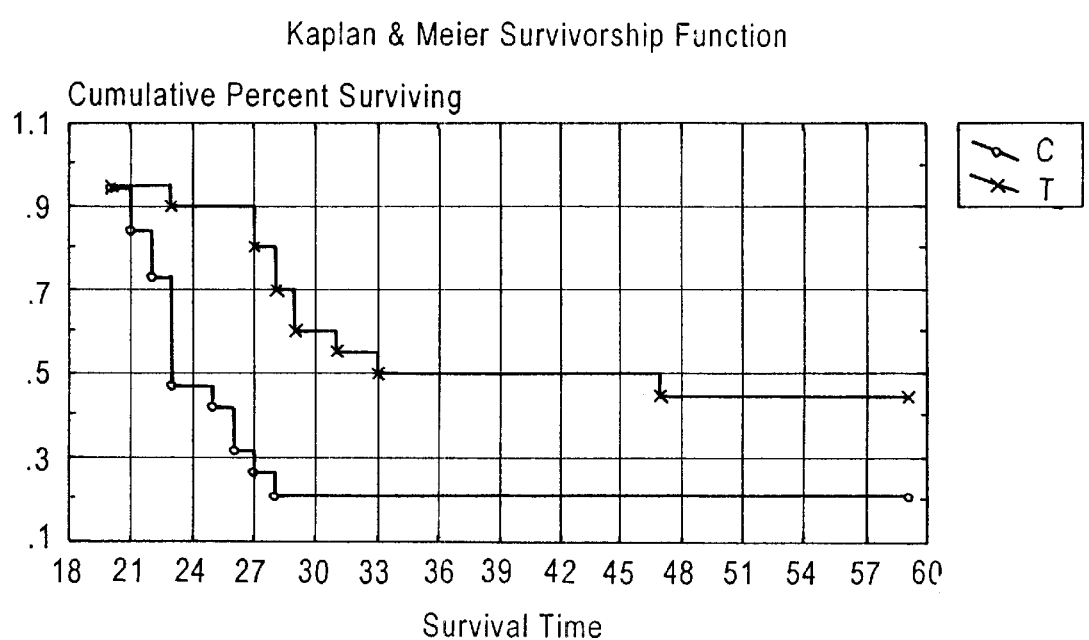

FIG. 5 is a graph illustrating the cumulative percentage of survival of mice treated with jasmonates to prevent the formation of lymphomas, versus untreated mice.

DETAILED DESCRIPTION OF THE INVENTION

It is appreciated that the detailed description that follows is intended only to illustrate certain preferred embodiments of the present invention. It is in no way intended to limit the scope of the invention, as set out in the claims.

The present invention describes use of jasmonates to prevent proliferation and induce death of malignant cells.

Particularly preferred jasmonates include jasmonic acid [(−)-JA and/or (+)-7-iso-JA], methyl jasmonate, jasmone, and 9,10-dihydro-jasmonic acid and its lower alkyl ester. Other preferred jasmonates include 4,5-didehydro-7-iso-JA, 3,7-didehydro-JA, cucurbic acid (CA), 6-epi-CA, 6-epi-CA-lactone, 12-hydroxy-JA, 12-hydroxy-JA-lactone, 11-hydroxy-JA, 8-hydroxy-JA, homo-JA, dihomo-JA, 11-hydroxy-dihomo-JA, 8-hydroxy-dihomo-JA, tuberonic acid (TA), TA-O-β-glucopyranoside, CA-O-β-glucopyranoside, amino acid conjugates of JA, as well as the corresponding lower alkyl esters of each of these acids.

The applicants have proven below, that two jasmonates, methyl jasmonate and jasmonic acid, have a positive therapeutic effect on malignant cells, yet do not harm normal cells such as normal circulatory lymphocytes. The following examples demonstrate that jasmonates are cytotoxic to four different types of malignant cells in culture, in doses that would be considered safe and attainable in mammals, and do not inhibit growth of healthy lymphocytes. The applicants have additionally proven, in Example 5, that jasmonates are effective in prolonging the lifetime of mice injected with lymphoma cells, resulting in a survival rate that is significantly higher than that of untreated mice (2.25 times the number of survivors than in the untreated group).

EXAMPLE 1

Plant Stress Hormones are Cytotoxic for Four Human Transformed Cell Lines

Four transformed cell lines of different histological lineages were exposed to one of three plant stress hormones. The cell lines chosen represent four types of cancer of widespread clinical importance. Molt-4 is a human T lymphoblastic leukemia cell line, SK-28 are human melanoma cells. LNCaP is an androgen-responsive human prostate adenocarcinoma cell line, and MCF7 is a human breast carcinoma cell line. All cell lines were purchased from ATCC (Rockville, Md.). All reagents were purchased from Sigma Chemicals (St. Louis, Mo.) unless otherwise stated. JA and MJ were dissolved in ethanol. All cell cultures were performed in RPMI-1640 with 10% fetal calf serum (Biological Industries, Beit-Haemek, Israel), and cells (except for Molt-4 and lymphocytes from the peripheral blood) were allowed to adhere prior to every treatment mentioned below.

LNCaP, MCF7 and SK-28 cells (at $4\times10^3$/well) and Molt-4 cells (at $1.5\times10^4$/well) were seeded in 96-well plates and allowed to adhere overnight. Plant stress hormone at increasing concentrations was added as indicated below, and toxicity was measured after 24 hours using the CellTiter 96 Aqueous Non-Radioactive Cell Proliferation Assay (Promega, Madison, Wis.); an assay in which viable cells produce a colored product (for details on the protocol of this assay, see below). This assay is quantitative, as the amount of color produced is read using an ELISA reader.

The highest non-toxic pharmacological concentration used in humans, of the nonsteroidal anti-inflammatory drug SA, is approximately 3 mM (Katzung, Lange Medical Book, Stamford, 1998). In order to compare the additional plant stress hormones JA (jasmonic acid) and MJ (methyl jasmonate) with SA, the same range of concentrations (0.5–3 mM) was chosen. These compounds at the aforementioned concentrations are not toxic for mice. Each cell line was incubated with each of these hormones at a concentration ranging from 0.5–3 mM for 24 hours, after which cytotoxicity was measured. The statistical significance of the results was determined (where appropriate) by two-tailed student's t-test, n=3. Results are presented as means ± standard deviation.

In reference to FIG. 1, the cytotoxicity of each one of three plant hormones is plotted as a measure of its concentration.

diamonds=Molt-4 lymphoblastic leukemia cells;
squares=SK28 melanoma cells;
triangles=LNCaP androgen-responsive prostate adenocarcinoma cells,
circles=MCF7 breast carcinoma cells.

Figure 1A:
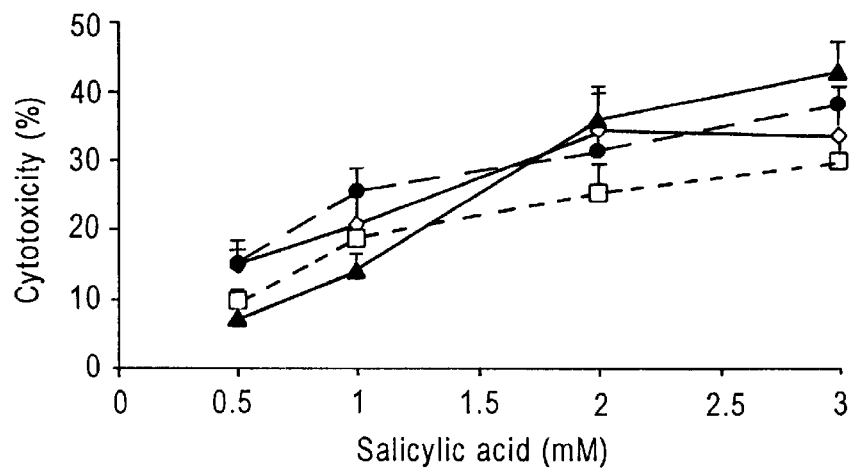
FIG. 1 is a graph illustrating the cytotoxicity of plant hormones methyl jasmonate and jasmonic acid, compared with salicylic acid, as a measure of their concentration.

Referring to FIG. 1A, all cell lines responded in a dose-dependent fashion to SA. Cytotoxicity of SA was significant, $P<0.05$, in Molt-4 lymphoblastic leukemia cells, SK28 melanoma cells and MCF7 breast carcinoma cells at all concentrations, and in LNCaP human prostate adenocarcinoma cells, from 1 mM and higher. SA was shown here to inhibit cell proliferation of different cancer cells from 20 to 40%, depending on the cell line. This finding is in agreement with similar reported observations, where SA inhibited growth of breast cancer cell lines, rat hepatoma and human fibroblasts cultures (Sotiriou et al., Anticancer Res., 19, 2997–3006 1999; Hial et al., J. Pharmacol. Exp. Ther., 202, 446–454 1977). A possible interpretation of this data is that SA causes stress in cancer cells, resulting in suppression of proliferation in those cells.

JA and MJ were studied in comparison to SA in order to determine whether the effects of SA on cancer cells are common to plant stress hormones, and whether jasmonates would be deemed more effective than salicylic acid at targeting and inhibiting the growth of malignant cells.

Figure 1B:
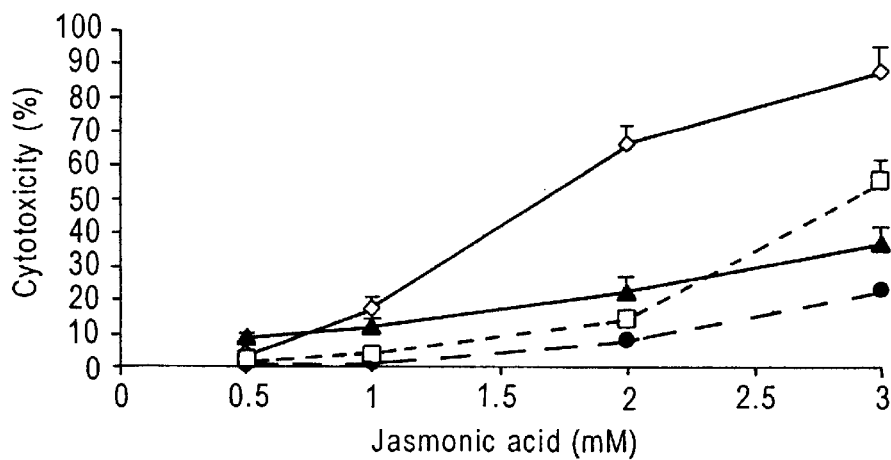

Referring to FIG. 1B, the responsiveness to JA was dose-dependent. The cytotoxicity of JA was significant, $P<0.05$, in Molt-4 cells from 1 mM and higher, in LNCaP and SK28 cells from 2 mM and higher, and in MCF7 cells at 3 mM. The order of sensitivity to JA was Molt-4>SK-28>LNCaP>MCF7.

Figure 1C:
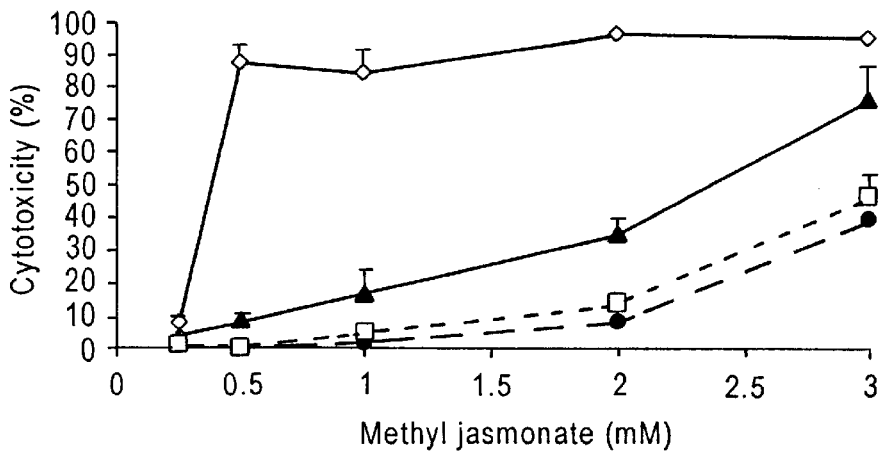

Referring to FIG. 1C, cytotoxicity of MJ was significant, $P<0.01$, in Molt-4 cells at all concentrations and in MCF7 cells at 3 mM; and at $P<0.05$ in LNCaP and SK28 cells from 2 mM and higher.

The results presented here show that MJ caused the highest level of cytotoxicity. For instance, 0.5 mM of MJ induced 87.52% cytotoxicity in Molt-4 cells. The other cell lines responded to MJ in a dose-dependent way. The order of sensitivity was Molt-4>LNCaP>SK28>MCF7.

Appropriate controls established that ethanol (in which JA and MJ were dissolved) by itself did not induce any cytotoxicity.

Example 1 demonstrates that while cancer cells from various origins responded to plant stress hormones, their response was differential. Among the cell lines examined, Molt-4 responded strongly to JA (90% cytotoxicity at 3 mM) and MJ (90% cytotoxicity at 0.5 mM).

Cytotoxicity Assay Used In Examples

Inhibition of cell proliferation was determined by the CellTiter 96 Aqueous Non-Radioactive Cell Proliferation Assay (Promega, Madison, Wis.): Upon completion of a given experiment, MTS (a tetrazolium compound) at 333 µg/ml + phenazine methosulfate (at 25 µM) was added to each well of the 96-well plate for 1 hour at 37° C. This allowed for development of a color reaction in which dehydrogenases reduce the MTS in metabolically active cells. Since the cells were not washed before the addition of MTS, there were no potentially loosely adherent or non-adherent cells that could have been problematic. Soluble MTS formazan product was measured at a wavelength of 490 nm using a CERES 900 HDI ELISA reader (Bio-Tek Instruments, Inc, Highland Park, Vt.). Optical density is directly proportional to the number of living cells in culture. Cytotoxicity (%) was calculated in the following way: [(OD of control cells−OD of drug-treated cells)/OD of control cells]×100.

EXAMPLE 2

Characterization of the Damage Induced by Jasmonates

Since the same number of cells was aliquoted into each well initially, decreased optical density as measured in wells containing treated cells (above) reflects cellular death and/or decrease in the rate of proliferation. To distinguish between these two possibilities we employed an additional cytotoxicity assay which detects cell death by lack of trypan blue exclusion. Cells were incubated with 0.1% trypan blue for 2–5 minutes and the percentage of dead cells (those, which did not exclude the dye) was determined microscopically.

Referring to Table 1, among the plant hormones tested, MJ induced death most effectively in every cell line. MJ is more effective in killing human transformed cell lines than its non-methylated form JA (FIGS. 1B, 1C and Table 1). SA suppressed proliferation in all cell lines, while JA induced death in lymphoblastic leukemia cells and suppression of proliferation in the other cells. In terms of relative susceptibility, Molt-4 cells are followed by SK28, LNCaP and MCF7 cells, in that order. Differential susceptibility of the different cell lines to the plant stress hormones suggests a specificity of the influence of those compounds on the cells.

It is important to note the difference between SA and jasmonates in their influence on cancer cell lines. SA causes inhibition of cell proliferation in the tested cell lines, JA causes cell death in Molt-4 cells and inhibition of cell proliferation in SK28, LNCaP and MCF7 cells, whereas MJ causes death in all cell lines. These differences could be explained by different structures of plant stress hormones and/or by difference in biochemical events that those compounds induce in the cells.

EXAMPLE 3

Jasmonates Induce Apoptosis in Molt-4 Cells

Elevated levels of Caspase-3 are a specific marker of the apoptosis process (Porter and Janicke, Cell Death Differ., 6, 99–104, 1999). In order to definitively determine that the cause of cell death was apoptosis, the level of Caspase-3 activity was measured in cells after treatment with JA and MJ.

Molt-4 cells were incubated with JA and MJ for 2, 4 and 14 hours, and levels of activity of the apoptosis-mediating protease, Caspase-3, were determined using the Caspase-3 (CPP32) protease assay kit (PharMingen, San Diego, Calif.) as suggested by the manufacturer. Briefly, $2 \times 10^6$ cells were lysed and resuspended in 100 µL of reaction buffer containing a fluorogenic Caspase-3 (CPP32) substrate Ac-DEVD-AMC. Reactions were incubated at 37° C. for 2 hours and samples were assayed at excitation wavelength of 360 nm and emission wavelength of 460 nm, in the FL600 Microplate Fluorescence Reader (Bio-Tek Instruments, Winooski, Vt., USA).

Referring to FIG. 2, dose-dependent elevation of Caspase-3 activity was observed:

(Diamonds=2 hours, squares=4 hours, triangles=14 hours.)

As can be seen in FIG. 2, JA and MJ increased Caspase-3 activity significantly, P<0.05, at all concentrations and times.

Figure 2A:
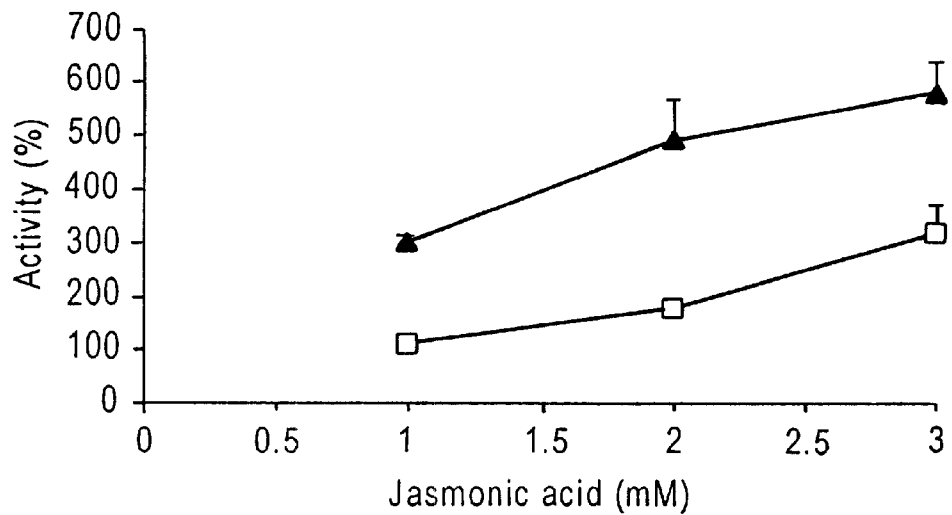

Referring to FIG. 2A, incubation with JA for 2 hours didn't induce an elevation in the level of Caspase-3.

Figure 2B:
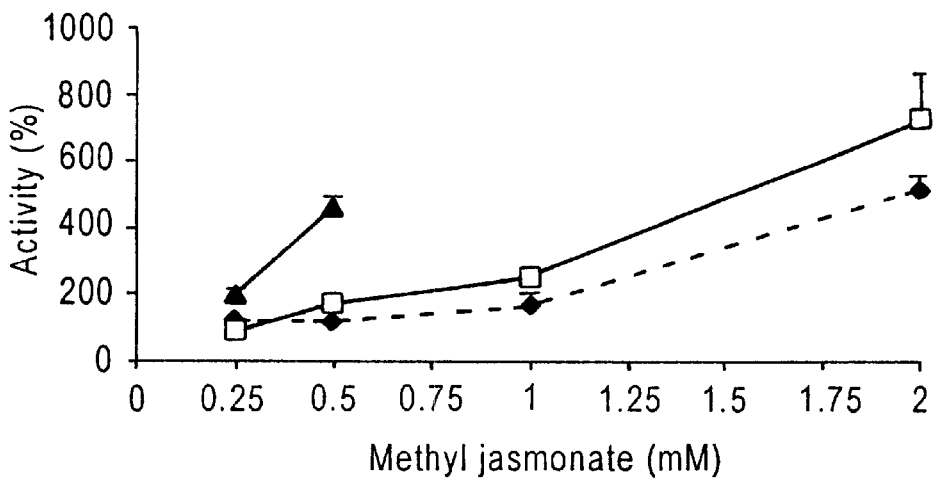

Referring to FIG. 2B, after 14 hours of exposure to MJ, the extent of death at 1 mM and above was such that Caspase-3 activity could not be determined.

These results suggested that JA and MJ induced apoptotic death in Molt-4 cells. To confirm this fact, Molt-4 cells were treated with JA (2 mM) and MJ (0.5 mM) for 14 hours, and analyzed by fluorescence microscopy in order to detect essential morphological characteristics of apoptosis such as condensation and fragmentation of chromatin.

Referring to FIG. 3, fluorescence microscopy pictures are shown depicting changes in cellular morphology within the nuclei of Molt-4 cells, after treatment with plant stress hormones JA or MJ. $5 \times 10^5$ cells/sample were harvested, then fixated by addition of a solution of phosphate-buffered saline (PBS) containing [3% paraformaldehyde and 0.1% Triton X-100], for one hour. Cells were stained for 10 minutes with DAPI (1 $\mu$g/ml). Nuclei were analyzed by fluorescence microscopy, (using a fluorescence microscope model. A×70 TRF, made by Olympus Optical, Japan) at a magnification of 1:400. Characteristic apoptotic nuclei are marked with arrows.

Referring to FIG. 3A, untreated Molt-4 cells are shown.

Referring to FIG. 3B, Molt-4 cells were treated with JA at 2 mM for 14 hours. Treatment with JA induced condensation and fragmentation of chromatin.

Referring to FIG. 3C, Molt-4 cells were treated with MJ at 0.5 mM for 14 hours. Treatment with MJ completely destroyed nuclear morphology in almost all cells.

These results confirm that JA and MJ caused apoptotic death in Molt-4 cells, based on the rise in caspase-3 activity, which is one of the features of apoptosis, and on characteristic morphological changes.

SA was reported to induce apoptosis and activation of caspases in myeloid leukemia cell lines and in B-cell chronic lymphocytic leukemia cells. There is also evidence that SA enhances apoptosis and causes apoptosis in FS-4 cells via p38 (Schwenger et al., Proc. Natl. Acad. Sci. USA, 4, 2869–2873, 1997). In those studies different cell lines undergo apoptosis on incubation with concentrations of salicylates higher than those achieved in plasma of patients treated for inflammatory disorders. In the present invention, concentrations of salicylates were used, that are comparable to those achieved in the plasma. This can explain the difference between studies where SA induced apoptosis, and our results.

EXAMPLE 4

Jasmonates are not Harmful to Normal Lymphocytes

The results shown above prove that plant stress hormones possess the ability to adversely affect cancer cells. The effect of these plant products was tested on normal cells, to determine if jasmonates have an adverse cytotoxic effect on non-cancerous cells as well.

Normal lymphocytes were separated from peripheral blood, as follows: Mononuclear cells (MNC) from venous blood of healthy donors were collected by Ficoll-Hypaque (Phamacia Fine Chemicals, Uppsala, Sweden) density gradient centrifugation. The resultant mononuclear cell preparation was allowed to adhere to plastic dishes to remove contaminant macrophages. The non-adherent peripheral blood lymphocytes were selected for use.

Prior to treatment with JA and MJ, normal lymphocytes were stimulated by TPA (5 ng/ml) and PHA (0.8 $\mu$g/ml) for 48 hours, to cause the lymphocytes to proliferate (and so, be comparable to the immortal malignant cells). Normal lymphocytes and Molt-4 cells were seeded (at $1.5 \times 10^4$/well) in 96-well plates.

Jasmonates or salicylic acid were added at a concentration of 1 mM or 3 mM, and cells were incubated for 24 hours. Optical density representing viable cells was determined by the CellTiter 96 Aqueous Non-Radioactive Cell Proliferation Assay.

Each plant stress hormone induced significant cytotoxicity in Molt-4 cells, P<0.05, while non of the hormones induced any significant cytotoxicity in normal lymphocytes.

Referring to FIG. 4, normal blood lymphocytes (represented by solid bars) were practically not influenced by plant stress hormones, contrary to the Molt-4 transformed lymphoblastic leukemia cells (represented by open bars).

Figure 4A:
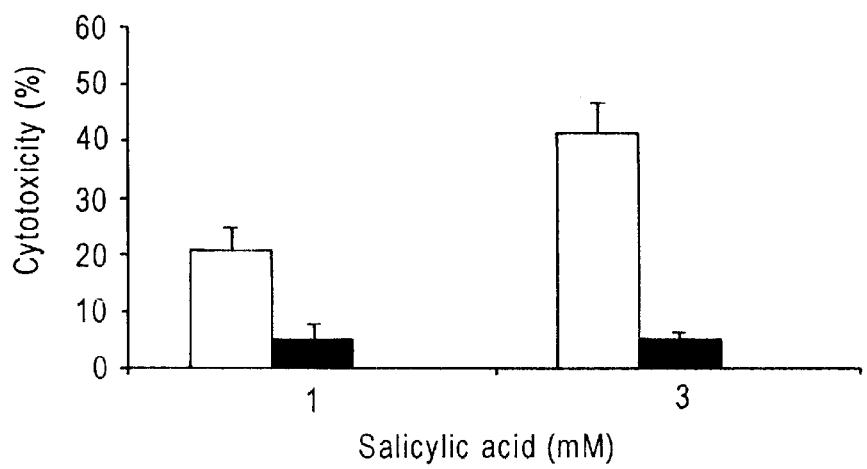

FIG. 4A shows treatment with SA at concentrations of 1 mM and 3 mM.

Figure 4B:
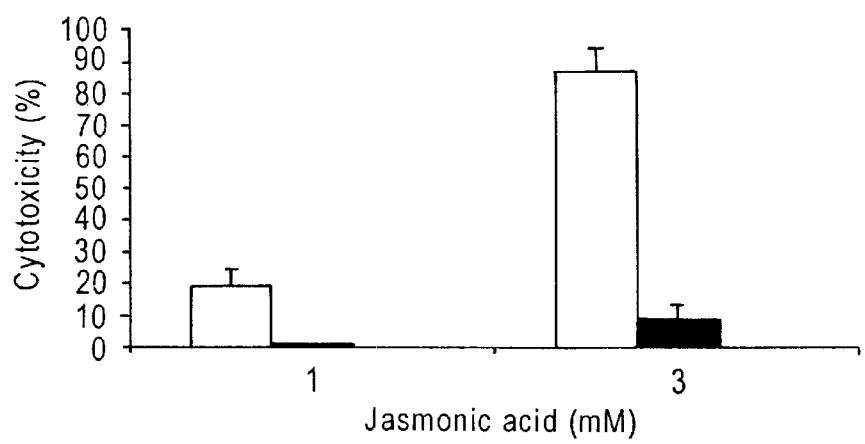
Figure 4C:
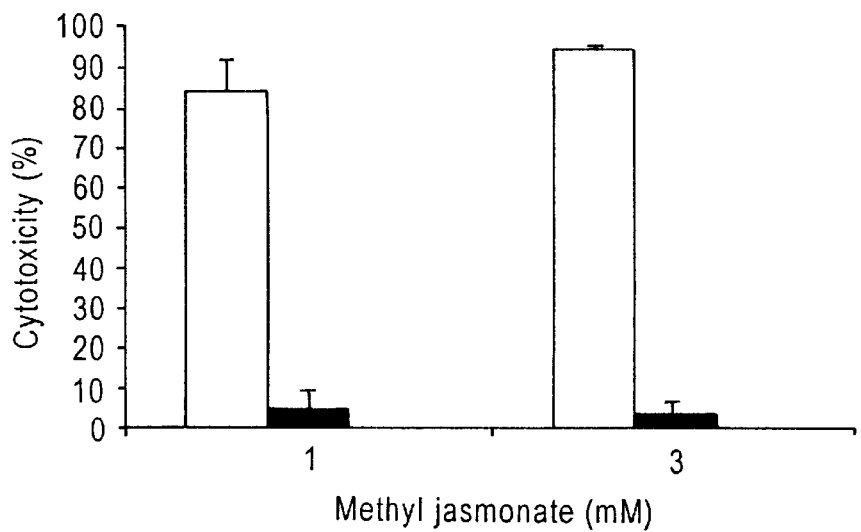

FIG. 4B shows treatment with JA at concentrations of 1 mM and 3 mM, and FIG. 4C shows treatment with MJ at concentrations of 1 mM and 3 mM.

Refer to Table 1 as well, which illustrates the selectivity of jasmonates for malignant cells versus healthy cells.

In this example, the influence of plant stress hormones on transformed lymphocytes (Molt-4 cells) was compared, versus their influence on normal lymphocytes extracted from peripheral blood. Normal lymphocytes (that had been stimulated by TPA/PHA to induce proliferation), were not influenced by SA and jasmonates, contrary to transformed lymphocytes. This data supports the potential use of plant stress hormones as selective anti-cancer agents.

EXAMPLE 5

In-vivo Experiments in Mice

Syngeneic lymphoma cells were injected into a test group and a control group of mice (strain C57BL). The injections were administered either sub-cutaneously, or intra-peritoneally. Methyl jasmonate was administered orally, by injection directly into the resultant tumor or into the peritoneum, and the effect on tumor progression and on the rate of survival, were analyzed.

400,000 EL-4 lymphoma cells were injected intra-peritoneally into 20 test mice, or 19 control mice, of the C57BL strain.

Preliminary experiments had shown that methyl jasmonate at a dosage of 236–472 mg/kg. body weight was appropriate for prevention of tumoral growth. Therefore, methyl jasmonate was dissolved in a lipid carrier (0.4% Lipofundin, manufactured by B. Brown, Melsunger, Germany) and administered orally at a dosage of 236 mg/kg body weight. Administration was daily, via the drinking water, beginning with the day of injection of the lymphoma cells.

19 control mice received the lipid carrier only (0.4% Lipofundin), with no methyl jasmonate dissolved within.

The survival time of each group of mice was measured (in days), and analyzed.

Referring to FIG. 5, a Kaplan & Meier Survivorship Function graph is shown, illustrating the cumulative percentage of survival in each group, as the experiment progressed. Survival rates were significantly higher for the treated group (represented by crosses, and by the letter "T"), versus the control group (represented by circles, and by the letter "C"); as can be seen, for example, in the plateau of 50% survival reached by the treated group on the 33$^{rd}$ day, as opposed to the plateau of 20% survival reached by the control group.

The significance of these results was analyzed statistically, using two highly stringent statistical means of analysis, the Log-Rank Test and the Cox-Mantel Test. Each of these tests weighs numerically the importance of a death within one of the two groups of mice, on a given day, compared to the number of surviving mice in the whole.

The significance of the results was deemed to be high, p=0.01492 for the Log-Rank Test, and p=0.00953 for the Cox-Mantel Test (wherein a result is considered significant if p<0.05).

In conclusion, Examples 1–5 elucidate the effect of the structurally-diverse plant stress hormones, jasmonates and salicylate, on cell proliferation and viability in several diverse cancer cell lines. There were four major findings. Firstly, all the stress hormones investigated share the ability to adversely affect proliferation of cancer cells. Jasmonic acid (JA) induced death in lymphoblastic leukemia cells and caused suppression of cell proliferation in the other human cancer cells mentioned above. Methyl jasmonate (MJ) induced death in each of the cell lines. The plant hormones acted dose-dependently in the following order of sensitivity: lymphoblastic leukemia>prostate cancer>melanoma>breast cancer. Secondly, death caused by jasmonates in Molt-4 cells was determined as apoptotic, similar to the mechanism most chemotherapeutic drugs employ at the cellular level. Thirdly, jasmonates do not cause damage to normal lymphocytes. Fourthly, jasmonates are effective not only in vitro, but also in an animal model of lymphoma, significantly increasing the survival rate (by 2.25 times), using a dosage deemed safe in mice.

These findings suggest that plant stress hormones may be used as a novel class of anti-cancer drugs.

What is claimed is:

1. A pharmaceutical composition useful for the treatment of cancer in mammals, comprising as an active ingredient a therapeutically effective amount of at least one jasmonate compound of the formula I:

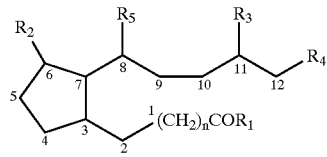

Formula I wherein:
n is 0,1, or 2;
$R_1$ is OH, alkoxy, O-glucosyl, or imino,
$R_2$ is OH, O, alkoxy or O-glucosyl,
$R_3$, $R_4$ and $R_5$ are H, OH, alkoxy or O-glucosyl,
and/or wherein $R_1$ and $R_2$, or $R_1$ and $R_4$ together form a lactone, and further wherein the bonds between $C_3$:$C_7$, $C_4$:$C_5$, and $C_9$:$C_{10}$ may be double or single bonds; or a derivative of said formula, wherein the derivative has at least one of the following:
a lower acyl side chain at $C_3$ (free acid or ester or conjugate), a keto or hydroxy (free hydroxy or ester) moiety at the $C_6$ carbon, or an n-pentenyl or n-pentyl side chain at $C_7$.

2. A composition according to claim 1, wherein the jasmonate is at least one member selected from the group consisting of methyl jasmonate, jasmonic acid, jasmone, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 6-epi-cucurbic-acid-lactone, 12-hydroxy-jasmonic acid, 12-hydroxy-jasmonic-acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydrojasmonic acid, 6,7-didehydro-jasmonic acid, 7,8-didehydrojasmonic acid, cis-jasmone, methyl-dihydro-isojasmonate, dihydro-jasmone, amino acid conjugates of jasmonic acid, the lower alkyl esters of said jasmonic acids, and the carrier ligand conjugates and the sterioisomers thereof.

3. A composition according to claim 1, wherein the active ingredient is dissolved in any acceptable lipid carrier.

4. A composition according to claim 1, additionally comprising at least one other chemotherapeutic agent.

5. A composition according to claim 1, wherein the composition is prepared for oral administration.

6. A composition according to claim 5, wherein the composition is in a form selected from an emulsion, a solution, a capsule, a tablet.

7. A composition according to claim 1, wherein the composition is prepared for administration by injection.

8. A composition according to claim 1, wherein the composition is prepared for topical administration.

9. A composition according to claim 8, wherein the composition is in a form selected from an ointment, a gel, or a cream.

10. A composition according to claim 1, wherein the composition is prepared for administration by inhalation.

11. A composition according to claim 1, wherein the composition is prepared for administration via suppository.

12. A method for treatment of non-prostate cancer in mammals comprising administering a pharmaceutical composition containing as an active ingredient a therapeutically effective amount of a jasmonate compound of Formula I:

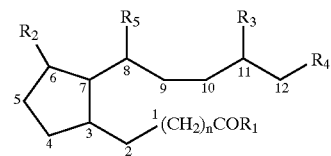

wherein:
n is 0,1, or 2;
$R_1$ is OH, alkoxy, O-glucosyl, or imino,
$R_2$ is OH, O, alkoxy or O-glucosyl,
$R_3$, $R_4$ and $R_5$ are H, OH, alkoxy or O-glucosyl,
and/or wherein $R_1$ and $R_2$, or $R_1$ and $R_4$ together form a lactone, and further wherein the bonds between $C_3$:$C_7$, $C_4$:$C_5$, and $C_9$:$C_{10}$ may be double or single bonds; or a derivative of said formula, wherein the derivative has at least one of the following:
a lower acyl side chain at $C_3$ (free acid or ester or conjugate), a keto or hydroxy (free hydroxy or ester)

moiety at the $C_6$ carbon, or an n-pentyl or n-pentyl side chain at $C_7$.

13. A method according to claim 12, wherein the jasmonate compound is at least one member selected from the group consisting of methyl jasmonate, jasmonic acid, jasmone, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 4,5-didehydro-7-iso-jasmonic acid, cucurbic acid, 6-epi-cucurbic acid, 6-epi-cucurbic-acid-lactone, 12-hydroxy-jasmonic acid, 12-hydroxy-jasmonic-acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydro-jasmonic acid, cis-jasmone, methyldihydroisojasmonate, dihydro-jasmone, amino acid conjugates of jasmonic acid, and the lower alkyl esters, the carrier ligand conjugates and the sterioisomers thereof.

14. A method according to claim 12, further comprising dissolving said active ingredient in a pharmaceutically acceptable lipid carrier and administering said solution to a mammal in a dose that is sufficient to treat cancer in said mammal.

15. A method according to claim 12, further comprising mixing at least one other chemotherapeutic agent into said pharmaceutical composition and and administering said mixture to a mammal in a dose that is sufficient to treat cancer in said mammal.

16. A method according to claim 12, further comprising preparing said composition for oral administration.

17. A method according to claim 16, further comprising emulsifying said composition in a pharmaceutically acceptable carrier.

18. A method according to claim 16, further comprising dissolving said composition in a pharmaceutically acceptable solvent.

19. A method according to claim 16, further comprising encapsulating said composition.

20. A method according to claim 16, further comprising further formulating said composition for administration as a tablet, making said tablet from said formulated composition and administering said tablet, containing a dose of said active ingredient that is sufficient to treat cancer in said mammal, to said mammal.

21. A method according to claim 16, further comprising further formulating said composition for administration by injection and injecting said injection formulated composition, containing a dose of said active ingredient that is sufficient to treat cancer in said mammal, into said mammal.

22. A method according to claim 16, further comprising formulating said composition as for topical administration and topically applying said topically formulated composition into direct contact with a cancer in said mammal.

23. A method according to claim 22, further comprising converting said composition into an ointment and directly applying said ointment onto said cancer.

24. A method according to claim 22, further comprising converting said composition into a gel and directly applying said gel onto said cancer.

25. A method according to claim 22, further comprising converting said composition into a cream and directly applying said cream onto said cancer.

26. A method according to claim 12, further comprising formulating said composition, containing a dose of said active ingredient sufficient to treat said cancer in said mammal, for administration by inhalation, and causing said mammal to inhale said inhalation formulated composition.

27. A method according to claim 12, further comprising formulating said composition, containing a dose of said active ingredient sufficient to treat said cancer in said mammal, for administration by suppository, and administering said suppository to said mammal.

28. A method according to claim 12, wherein said cancer is at least one member selected from the group consisting of breast cancer, skin cancer, colon cancer, lung cancer, pancreatic cancer, lymphoma, leukemia, head and neck cancer, kidney cancer, ovarian cancer, bone cancer, liver cancer and thyroid cancer.

29. A method according to claim 12 further comprising administering said composition to said mammal in a dose that is sufficient to treat said cancer but is insufficient to harm a substantial proportion of tissue proximate to said cancer.

30. A method according to claim 12 wherein said cancer is at least one selected from the group consisting of: breast cancer, skin cancer, colon cancer, pancreatic cancer, lymphoma, leukemia, head and neck cancer, kidney cancer, ovarian cancer, bone cancer, liver cancer and thyroid cancer.

31. The method according to claim 30 wherein said cancer comprises cancerous cells that are not dependent on the effective presence of androgens for cell growth.

32. A composition according to claim 1 containing an amount of said active jasmonate ingredient that is sufficient to treat said cancer but insufficient to materially adversely affect non-cancerous tissue.

\* \* \* \* \*